United States Patent
Yoon et al.

(10) Patent No.: US 11,107,854 B2
(45) Date of Patent: *Aug. 31, 2021

(54) USE OF SURFACE PATTERNING FOR FABRICATING A SINGLE DIE DIRECT CAPTURE DENTAL X-RAY IMAGING SENSOR

(71) Applicant: Cyber Medical Imaging, Inc., Los Angeles, CA (US)

(72) Inventors: Douglas C Yoon, Los Angeles, CA (US); Oscar Magnus Stafsudd, Los Angeles, CA (US)

(73) Assignee: CYBER MEDICAL IMAGING, INC., Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/132,004

(22) Filed: Dec. 23, 2020

(65) Prior Publication Data

US 2021/0111219 A1     Apr. 15, 2021

Related U.S. Application Data

(63) Continuation of application No. 16/929,290, filed on Jul. 15, 2020, now Pat. No. 10,910,432.

(60) Provisional application No. 62/877,819, filed on Jul. 23, 2019.

(51) Int. Cl.
*H01L 27/146* (2006.01)
*A61B 6/00* (2006.01)
*G01T 1/24* (2006.01)
*H01L 31/0368* (2006.01)
*H01L 31/0296* (2006.01)
*A61B 6/14* (2006.01)

(52) U.S. Cl.
CPC ...... *H01L 27/14676* (2013.01); *A61B 6/4233* (2013.01); *G01T 1/246* (2013.01); *G01T 1/247* (2013.01); *H01L 27/14696* (2013.01); *H01L 31/0296* (2013.01); *H01L 31/0368* (2013.01); *A61B 6/14* (2013.01)

(58) Field of Classification Search
CPC ......... H01L 27/14676; H01L 27/14696; H01L 31/0296; H01L 31/0368; G01T 1/246; G01T 1/247; A61B 6/4233; A61B 6/14
See application file for complete search history.

(56) References Cited

U.S. PATENT DOCUMENTS

| | | | | |
|---|---|---|---|---|
| 7,456,409 | B2 * | 11/2008 | Dhurjaty | G01T 1/17 250/369 |
| 7,547,889 | B2 * | 6/2009 | Lehmann | G01T 1/17 250/370.01 |
| 2018/0059265 | A1 * | 3/2018 | Zhang | G01T 1/241 |

* cited by examiner

*Primary Examiner* — Michael C Bryant
(74) *Attorney, Agent, or Firm* — Roy L Anderson

(57) ABSTRACT

A device and process in which a single continuous depositional layer of a polycrystalline photoactive material is deposited on an integrated charge storage, amplification, and readout circuit with an irregular surface wherein the polycrystalline photoactive material is comprised of a II-VI semiconductor compound or alloys of II-VI compounds.

27 Claims, 6 Drawing Sheets

USE OF SURFACE PATTERNING FOR FABRICATING A SINGLE DIE DIRECT CAPTURE DENTAL X-RAY IMAGING SENSOR

CROSS REFERENCE TO RELATED APPLICATION

This application is a continuation of U.S. Ser. No. 16/929,290, filed Jul. 15, 2020, the disclosure of which is specifically incorporated herein by reference in its entirety.

FIELD OF THE INVENTION

The field of the invention is digital intraoral radiography and the fabrication of solid-state sensors used in acquiring digital radiographic images.

BACKGROUND OF THE INVENTION

Over the last 20 years, dentistry has experienced an evolutionary shift from film-based radiography to computer-based digital radiography. At the heart of this evolution has been the application of silicon based solid-state integrated circuit (IC) technology to dental intraoral radiography. The current approach has been to retrofit silicon based visible light imaging chips (or dies) to the medical X-ray regime.

Visible light imaging chips exploit the fact that silicon, with an atomic weight of 28 and a band gap energy of 1.1-1.2 eV, readily interacts with visible-light photons to produce charge carriers through the generation of electron hole pairs. Therefore, it is relatively straightforward to create on a single silicon die circuitry organized into large arrays of individual pixels, each incorporating components for photodetection (e.g. photoresistors, photodiodes, photocapacitors, etc.), as well as components for charge storage, amplification, and readout. Even though the circuitry created by current techniques on the surface of a silicon wafer is only a few microns thick, this is sufficient for the photodetector component to operate under a wide range of visible light illumination levels. Visible light imaging chips are called 'direct photon capture' devices because photons striking the photodetector component of the IC directly lead to the production of charges in proportion to the illumination level.

Unfortunately, silicon's absorption in the medical X-ray regime (which generally have energies in the 50-70 keV range) is very low, due primarily to its low atomic number (Z) and would therefore require thicknesses on the order of 1 or more millimeters for sufficiently high efficiency. Note that high efficiency is required in medical applications in order to keep patient X-ray doses within safe levels. Thus, imaging chips that work for visible light will not work with X-rays, and solutions have been sought that use materials with significantly higher Z than silicon as the main photoactive material in the photodetector.

The currently adopted solution for dental intraoral radiography is to retrofit a visible light imaging chip by placing a fluoroscopic screen or scintillator in front of the chip. This approach is often referred to as 'indirect photon capture' because the photodetector is not directly part of the pixel circuitry. That is, X-ray photons are first captured and ultimately converted to visible light photons, rather than charges, by a scintillator layer made of high-Z materials such as cesium iodide (CsI) or gadolinium oxysulfide ($Gd_2O_2S$) through the process of fluorescence. The visible light photons are then captured by conventional silicon-based visible light imaging devices such as CCD, CMOS or TFT-based imaging chips. There is no focusing of the visible light image produced on the surface of the scintillator due to the excessive bulk of a lensing system (these devices need to fit into the mouth). Rather, image transfer is achieved through direct contact between the scintillator and the imaging chip.

The use of a scintillator has a number of drawbacks, which include the following issues. First, the fidelity of image transfer depends on good optical coupling between the two layers, which in turn requires intimate contact, much like a film negative to photographic paper in a photographic contact print. Limitations in optical coupling result in some image degradation. Second, because fluorescence is omnidirectional, the visible light photons produced by the scintillator layer are emitted in all directions, producing image blurring. This is further exacerbated by internal scattering and other effects within the scintillator. These effects are significant because the scintillators must be quite thick (100-300 microns) for sufficient capture efficiency despite the high atomic weight of these materials. There have been some attempts to constrain the direction of photons to underlying pixels, e.g., by using columnar CsI as the scintillator, which tends to act as a waveguide. However, this does not completely eliminate the problem. Third, scintillator delamination and other deterioration can occur through rough handling and exposure to moisture, thus degrading the physical device. Furthermore, the manufacture the scintillation layer and its integration with a visible light imaging chip is a time-consuming and costly multi-step process, with many potential points of failure, making it both economically and technically disadvantageous.

Methods have been sought to incorporate high Z photoactive materials (such as materials that produce charge under illumination) within the circuitry of the imaging chip to allow for direct photon capture. Current methods recognize the difficulty and cost of creating complex electrical components (such as photodetectors) 100-300 microns deep concurrent with the silicon-based circuitry on the surface of a wafer (generally less than 10 microns deep). Thus, it is necessary to create the photodetector components of each pixel in a separate thick layer. For example, very thick layers of polycrystalline cadmium telluride (CdTe) up to 100-300 microns have been grown for use in large format dental X-ray imagers, such as panoramic and conebeam (3-D) imaging systems. The key has been the use of high depositional temperatures in excess of 500 degrees C. Temperatures above about 500 degrees C. are generally considered destructive to silicon circuitry, such as CMOS, CCD, or TFT, and temperatures below about 350 degrees C. are generally considered to be safe. In the range between 350 and 500 degrees C., the general rule is the longer the exposure the greater the risk of damage to the circuitry. Developers overcame the problem of high depositional temperatures by fabricating the CdTe photodetector component of the imager on a separate substrate and under different conditions from the rest of the imager circuitry (e.g., charge storage, amplification, and readout components). Dies produced from the two substrates were then aligned and physically and electrically bonded in a process known as flip chip bonding. Limits in the precision of bonding limits the size of imaging pixels to a larger size and is a time-consuming expensive process. If somehow the CdTe could be deposited with sufficient thickness directly on the surface of the silicon-based circuitry then the use of multiple dies could be avoided. But currently no sensors incorporating this idea have been produced. The problem has historically been the difficulty of depositing physically and electrically stable adherent layers of sufficient thickness upon silicon-based substrates. As layer thickness grows the effects of differences in thermal expansion, crystal defects, cracks, pealing, impurities, etc. also become more pronounced, ultimately limiting the thickness below desired levels. For example, 10 microns has usually been considered the ultimate limit for the thickness of polycrystalline CdTe, based on years of research in the photovoltaics industry. 10 microns would produce capture efficiencies far below that of current "indirect capture" sensors.

Accordingly, there has been a long-felt need for a means of depositing very thick layers of photoactive materials, such as CdTe, directly on the surface of silicon circuitry that is electrically and physically stable. The present invention satisfies this long-felt need.

SUMMARY OF THE INVENTION

The present invention is generally directed to a device in which an integrated charge storage, amplification, and readout circuit serves as a depositional substrate with an irregular surface while a polycrystalline photoactive material is deposited as a single continuous depositional layer on top of the integrated charge storage, amplification, and readout circuit and the polycrystalline photoactive material is comprised of a II-VI semiconductor compound or alloys of II-VI compounds.

The present invention is also generally directed to a process in which a single continuous depositional layer of a polycrystalline photoactive material is deposited on an integrated charge storage, amplification, and readout circuit serving as a depositional substrate with an irregular surface wherein the polycrystalline photoactive material is comprised of a II-VI semiconductor compound or alloys of II-VI compounds.

The present invention is also generally directed to a sensor useful for detecting X-ray photons having a silicon-based single die, charge storage, amplification, and readout pixel array integrated circuit serving as a depositional substrate with an irregular surface with a polycrystalline photoactive material deposited as a single continuous depositional layer on top of the integrated charge storage, amplification, and readout circuit, wherein the periodic pattern is a non-planar surface with two or more alternating elevations at a minimum difference of at least approximately 0.1 micron and a maximum difference of approximately 100 microns while the prescribed size has a distance of repetition of at least approximately 1 micron but at most 100 microns; wherein the polycrystalline photoactive material is selected from the group consisting of CdTe, $Hg_xCd_{(1-x)}Te$, and $Zn_xCd_{(1-x)}Te$ and wherein the single continuous depositional layer has a total surface area which exceeds 500 square millimeters.

Accordingly, it is an object of the present invention to provide improvements in digital intraoral radiography by the fabrication of solid-state sensors used in acquiring digital radiographic images in which very thick layers of photoactive materials, such as CdTe, are deposited directly on the surface of silicon circuitry that is electrically and physically stable.

This and further objects and advantages will be apparent to those skilled in the art in connection with the drawings and the detailed description of the invention set forth below.

BRIEF DESCRIPTION OF THE DRAWINGS

FIGS. 1 and 1A are a whole wafer and close-up schematic view, respectively, which illustrate a sample textured depositional surface used in accordance with the present invention.

DETAILED DESCRIPTION OF THE INVENTION

Figure 1:
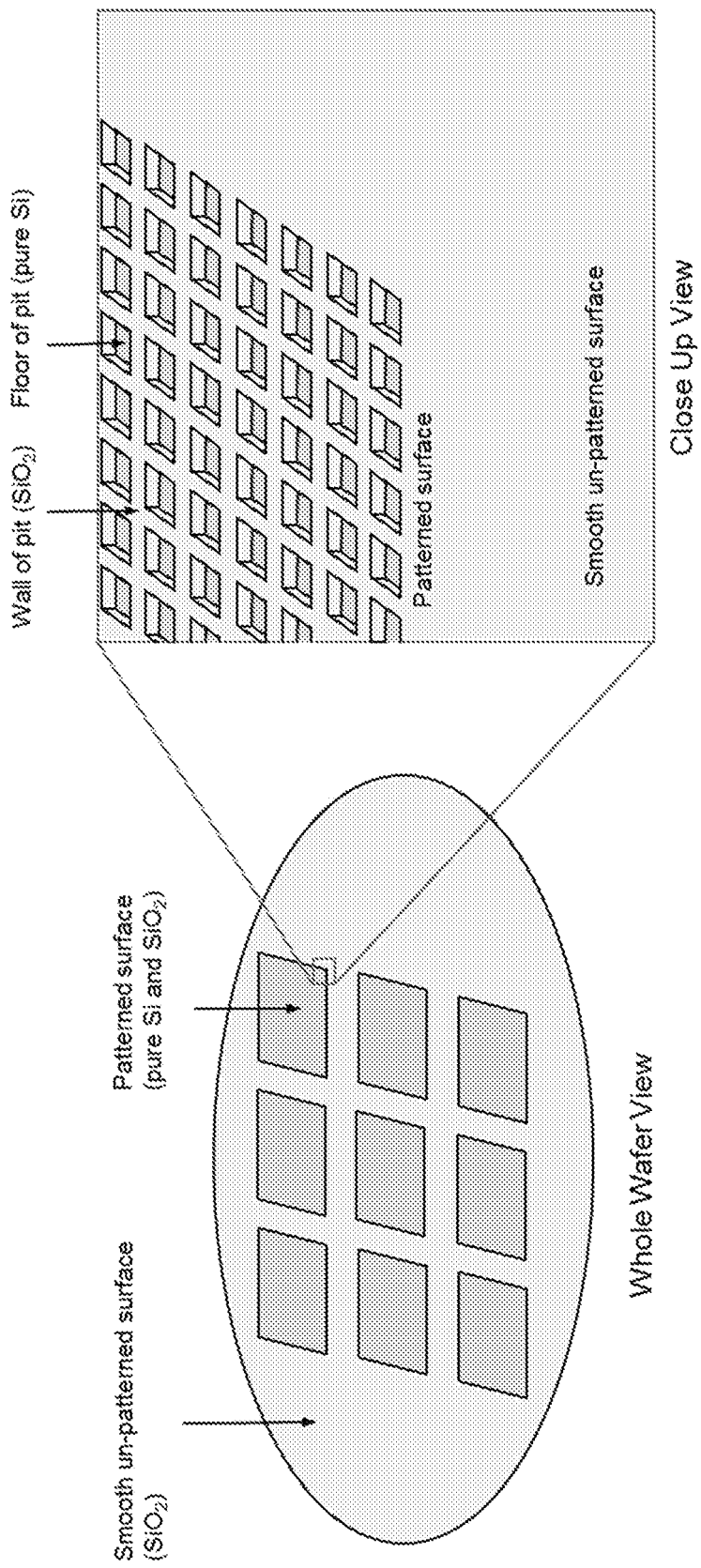

The present invention challenges the current wisdom that circuit substrates be smooth and defect free. This stems from a number of requirements including epitaxial growth, limitations in masking technology, circuit continuity, chip bonding, etc. The present invention provides a means of creating a sufficiently thick layer of photoactive material, preferably polycrystalline cadmium telluride (CdTe) directly on the surface of an integrated circuit, preferably a silicon based integrated circuit (e.g. CMOS, CCD, TFT). The photoactive material is in direct electrical contact with the pixel circuitry below. The current invention employs an alternate circuit substrate surface structure that facilitates the deposition of a high Z photoactive material onto the surface of the integrated circuit in a single chip architecture at relatively low substrate temperatures, i.e. below 350 degrees C., to avoid any possible degradation of the readout electronics. This avoids the more complex process of fabricating the different layers separately and then bonding them together, thus reducing fabrication costs and complexity, and increasing durability by having fewer bonded components.

The current invention intentionally creates an irregular ('bumpy') surface of an integrated circuit, preferably silicon based, as the depositional substrate of a high Z photoactive material, preferably polycrystalline II-VI semiconductor compounds and their alloys such as CdTe, $Hg_xCd_{(1-x)}Te$, $Zn_xCd_{(1-x)}Te$, and $A_xB_{(1-x)}C$ generically. The irregularities consist of variations in elevation. The boundary of different elevations serves as attractive seeding locations for crystal formation and anchoring, therefore improving adhesion, due to increased points of contact which enhances Van der Waals or other attractive forces. The optimal spacing of the boundary interfaces need to be determined experimentally based on the materials used and the depositional conditions. The current invention is therefore an alternative to the use of a separate intermediate layer between the integrated circuit and the photoactive material to enhance adhesion.

A set of experiments were conducted to test the general theory on silicon wafers whose surfaces were specially prepared to present variations in surface height with a regular spacing. A standard silicon wafer with a 1-micron thick layer of $SiO_2$ created on the surface was used. Note, that in this experiment the irregular surface was heterogenous in composition, yet the concept of enhanced attraction still pertains. Square pits were etched through the $SiO_2$ layer down to bare silicon to a depth of 1 micron or slightly greater. The pits were arranged in a rectangular grid and created a "waffle" like appearance, a small sub-section, a sample of which is illustrated in FIG. 1A. In this sample the entire "waffle" structure was 2 cm by 2 cm with 20 micron spacing between the square pits, there being a repeating pattern of insulating walls (in this sample 5 microns wide and 1 micron high) surrounding square pits (in this sample 15 microns by 15 microns and 1 micron deep) with conductive floors. The surface of the bottoms of the "waffle" pits consisted of pure silicon but the walls between the waffle pits consisted of $SiO_2$. Samples of grids with different pit sizes and spacings were created.

CdTe films were then deposited upon these surfaces according the following protocol. First the wafers were cleaned by standard semi-conductor cleaning techniques ending in a BOE etch. Immediately after BOE etch the samples were placed into a thermal evaporation chamber. The background chamber was between $10^{-5}$ and $10^{-6}$ Torr. Argon gas was then introduced into the chamber to approximately $4 \times 10^{-1}$ Torr and a plasma discharge was initiated for final cleaning. Subsequently background pressure was again reduced to a range between $10^{-5}$ and $10^{-6}$ Torr. Immediately after cleaning CdTe deposition was performed at a prescribed substrate temperature and deposition rate. A series of runs were performed in which films were deposited at substrate temperatures of 100, 150, and 200 degrees C. and at deposition rates of approximately 2, 5, 10 and 15 minutes per micron. The CdTe source was sublimated by a variable output radiant heat source. Deposition rates were monitored by an IR interferometer. Films as thick at 70-80 microns were produced and this was accomplished at substrate temperatures considerably below the 350 degrees C. temperature considered safe for silicon-based circuitry.

Figure 2:
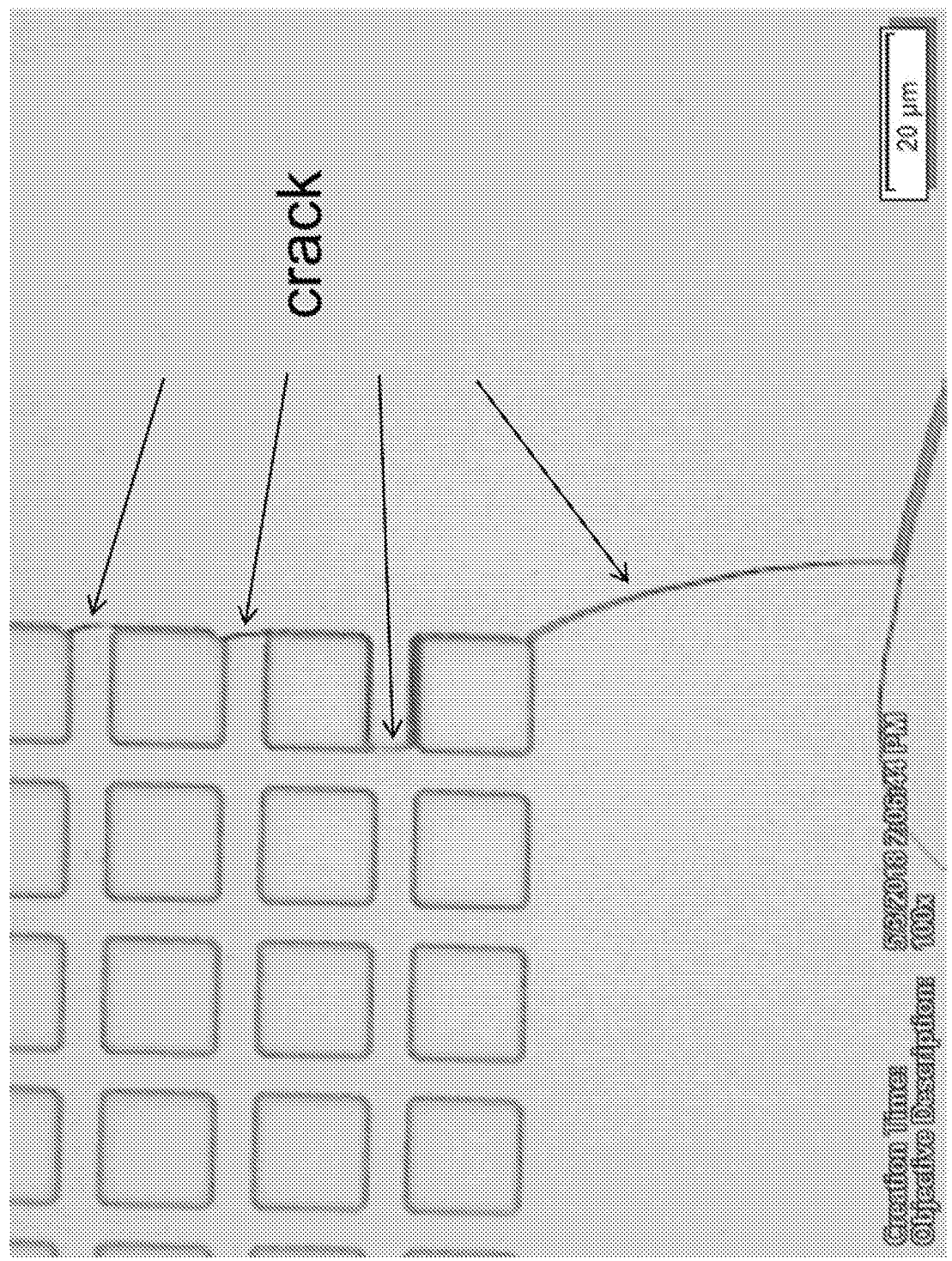
FIG. 2 is a micrograph (100×) of CdTe film surface on a wafer at one corner of the repeating pattern illustrated in FIG. 1.

In another set of experiments, it was discovered that pit spacings of approximately 100 microns or less exhibited enhanced adhesion (no pealing) and crack resistance, with no further advantage at less than 20 microns spacing. FIG. 2 shows examples of cracks originating in a non "waffle" region of the wafer propagating to the first of the waffle pits only and going no deeper into the pattern. In this case a crack originating in the un-patterned region proceeds into the first pit on the edge of the pattern and continues at the outer edge but proceeds no deeper into the patterned region. This behavior was a general result indicating that the pattern increased adhesion but also terminated cracks. Significant pealing was observed in the un-patterned areas. Months after deposition the films remained stable over the patterned regions for both sets of experiments.

Figure 3:
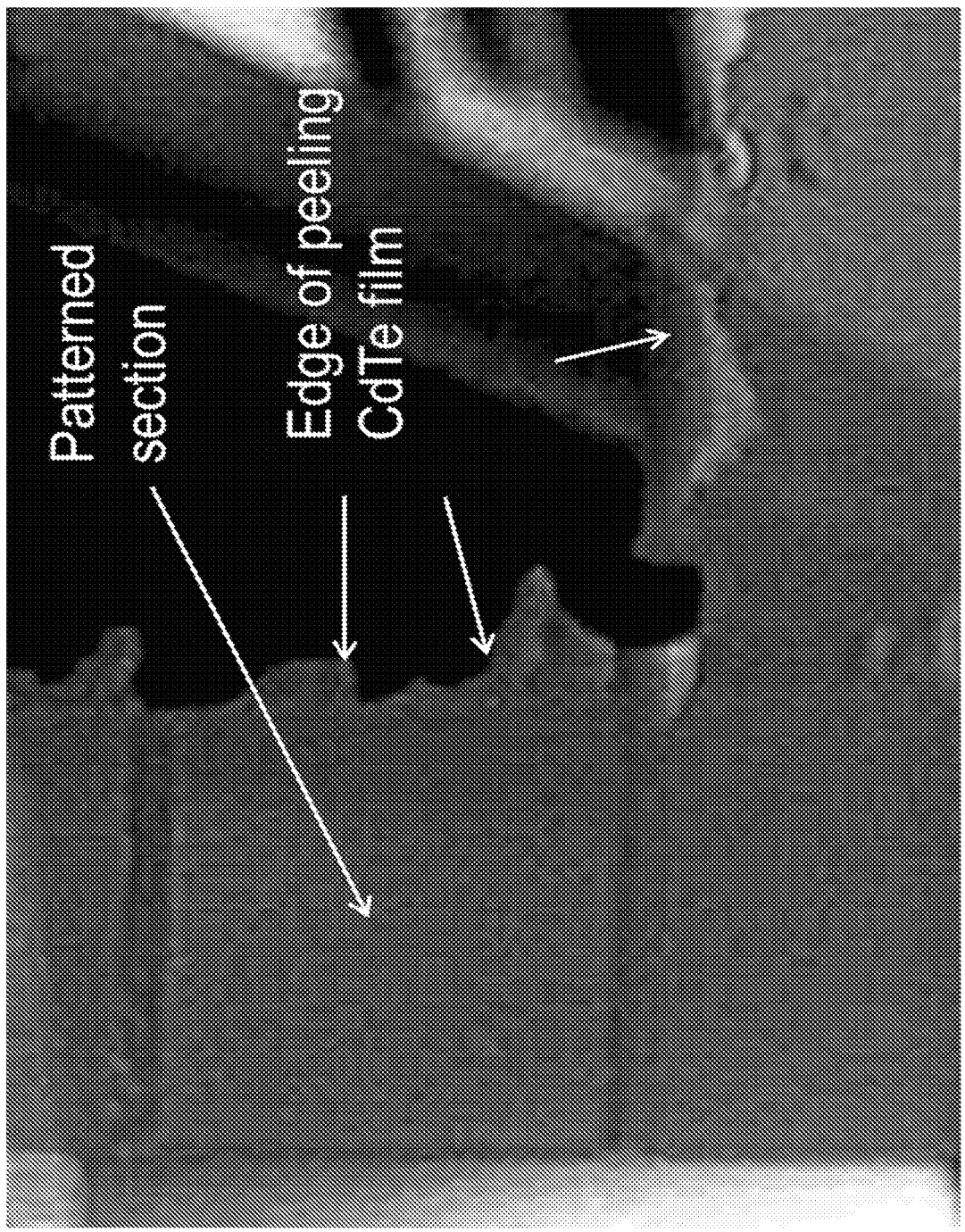
FIG. 3 is a macroscopic view showing enhancement of adhesion of CdTe (gray areas) in square regions of patterning (3 mm×3 mm) similar to that shown in FIG. 1 and delamination or peeling of CdTe over un-patterned regions (shiny areas).

These experiments suggest a modification of X-ray sensor integrated circuit design that will take advantage of this phenomenology. This is illustrated in FIG. 3 showing in cross section the circuitry for two adjacent pixels. By standard fabrication techniques pixel circuitry can be created within the surface of a silicon wafer that includes all the components of a typical visible light imager except the photodetector component. Instead, a conductive path is created from the charge storage component to the surface of the wafer creating a conductive region within the surface of each pixel. To protect underlying circuitry and prevent electrical shorts between adjacent conductive regions insulating walls are created between the conductive regions. This can be easily created by depositing a continuous layer of insulating material such as $SiO_2$ over the entire wafer surface and then etching isolated pits down to the conductive regions resulting in a pattern as shown in FIG. 1.

Figure 5:
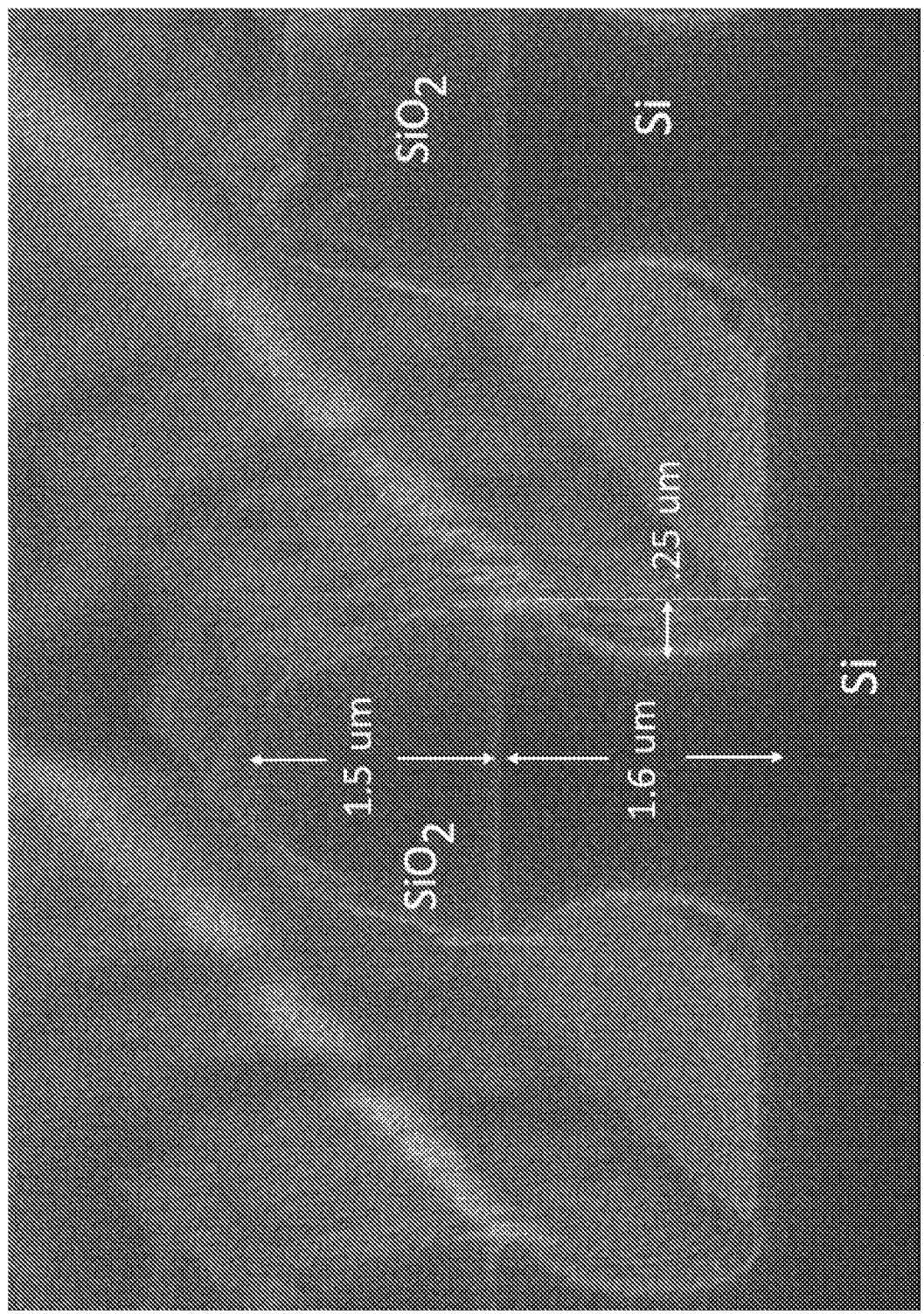
FIG. 5 is a scanning electron micrograph (SEM) of a wafer cut in cross-section through specially prepared troughs exhibiting undercut walls (0.25 microns as shown) down into the silicon substrate.

Further, the etching of the $SiO_2$ can be modified with techniques to purposefully create undercuts in the walls of the "waffle" pits to create mechanical retention, significantly increasing adhesion beyond that created by van der Waals forces alone. FIG. 5 shows a SEM of a specially prepared wafer sample in which undercut walls have been created. Such undercuts create mechanical retention for the photoactive material deposited on this surface. This specific sample was created using a combination anisotropic and isotropic dry etching techniques on a silicon wafer with a surface coating of $SiO_2$. In this example, an anisotropic etching technique was first used to etch preferentially vertically down to the silicon layer. Then, an isotropic etching technique, that was selective for pure silicon, was used to etch laterally as well as downward. The lateral component of this second etching created an undercut into the pure silicon and under the etch resistant $SiO_2$. In general, undercuts can be created by exploiting differences in etching rates of the different structural layers of a wafer and by exploiting combinations of anisotropic versus isotropic etching techniques.

Note that in the specially prepared sample shown, troughs rather than pits were used. This was to ensure that the wafer could be reliably sectioned at right angles through a wall to show the undercuts in a SEM of the cross section. Similar undercuts would be created for pits as well.

Figure 4:
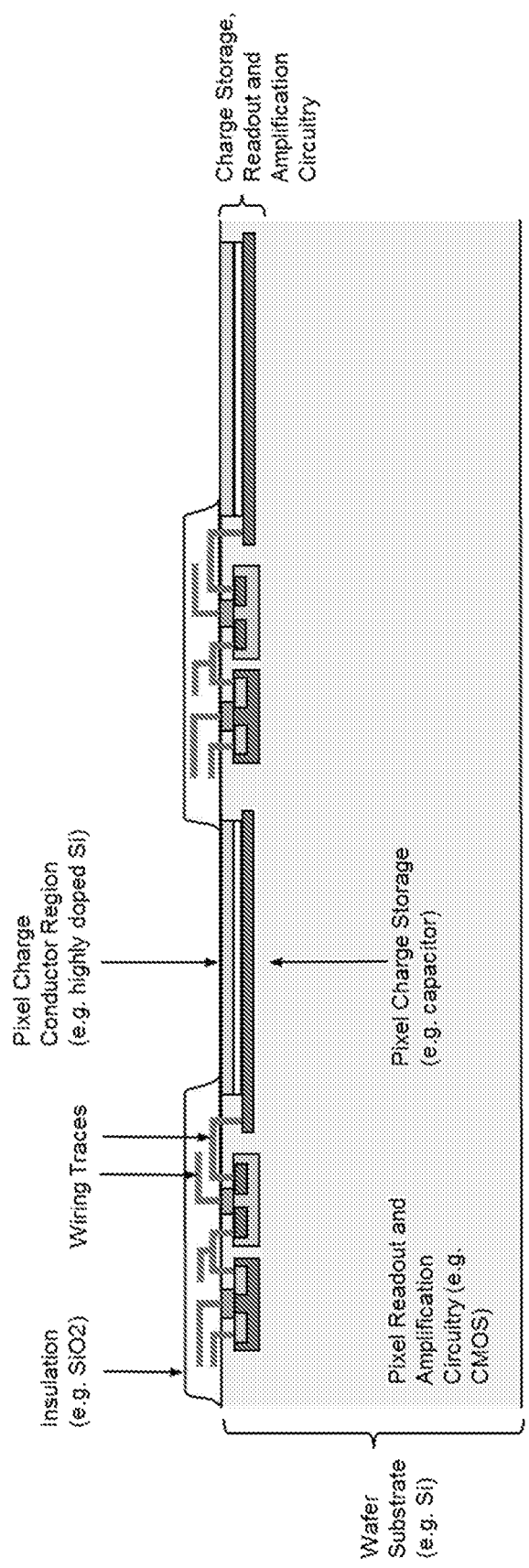
FIG. 4 illustrates an example of a CMOS circuit substrate for deposition (circuit components and layer thicknesses not drawn to scale). Insulation between pixels creates a repeating surface pattern consisting of alternating elevations and materials similar to that shown in FIG. 1.
Figure 6:
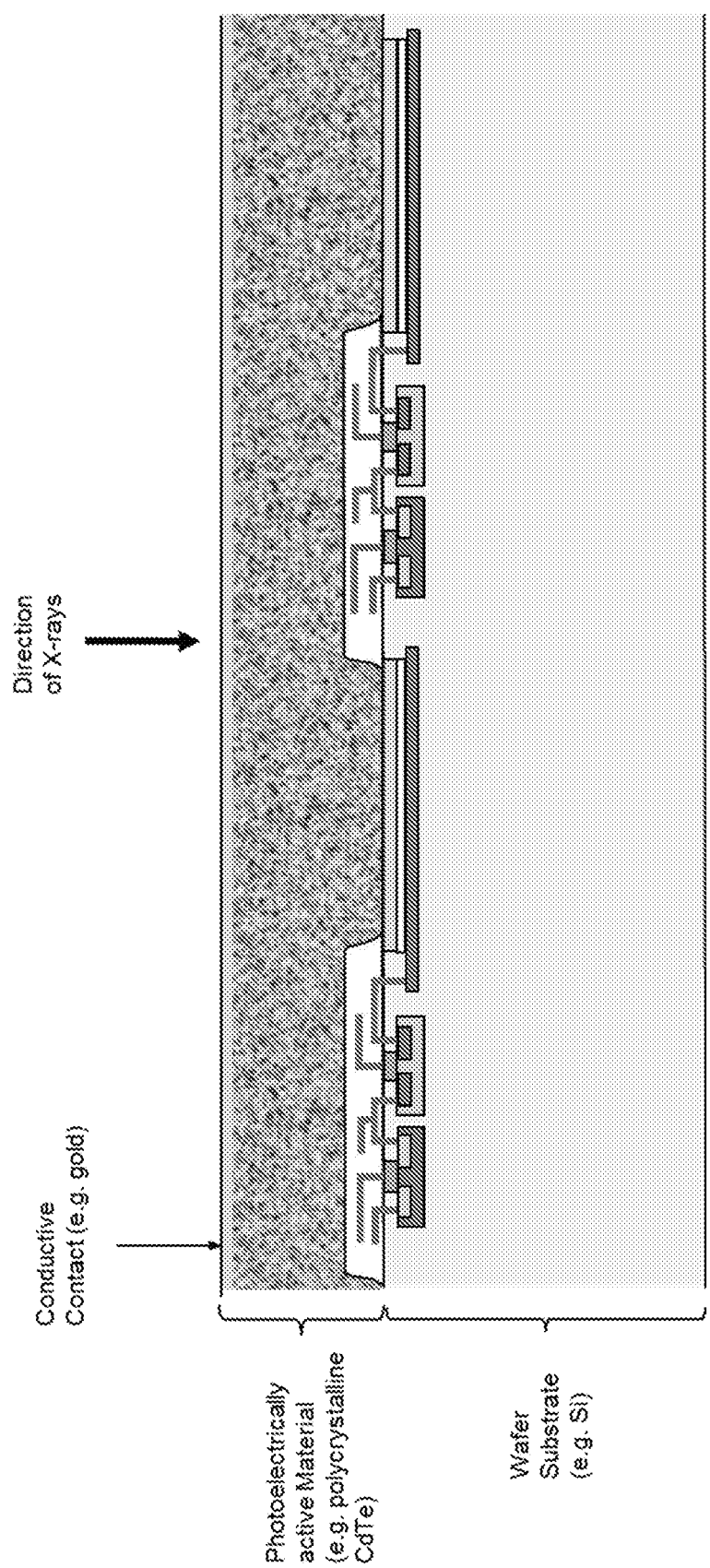
FIG. 6 illustrates a completed X-ray imager with photoactive material directly deposed on the patterned surface of example CMOS circuit (circuit components and layer thicknesses not drawn to scale).

The structure shown in FIG. 4 then serves as the substrate upon which to directly deposit the photoelectrically material in electrical contact with each conduction region in the array with the completed structure looking something like FIG. 6. In a preferred embodiment this material will be polycrystalline CdTe or one of its alloys (such as CdTe, $Hg_xCd_{(1-x)}Te$, $Zn_xCd_{(1-x)}Te$). This layer is grown to the appropriate thickness depending upon photoelectrical properties of the material. For CdTe, for example, 100 to 300 microns provides sufficient quantum efficiency and spatial resolution. This layer is directly deposited on normal silicon charge storage, amplification, and readout electronics by a number of means including, but not exclusive to, thermal evaporation, argon beam sputtering, e-beam evaporation, and chemical deposition. In the preferred embodiment the resulting photodetectors are functioning as photodiodes whose resistance decreases proportionally under X-ray illumination. CdTe has the advantage of high resistance and hence low current leakage (dark current) when not under illumination and relatively higher resistance in the lateral (or tangential) direction due to its columnar polycrystalline structure, helping to reduce pixel cross talk.

Finally, a thin conductive contact (such as gold or other metallization) to the photodetector devices is created on the top surface of the photoactive layer. By applying an appropriate voltage bias to the conductive contact, the resulting electric field preferentially drives charges to the conduction regions below, before the charge pairs can be destroyed by recombination, and thus helps to reduce pixel cross talk. Note that the X-ray photons will easily pass through the thin conductive contact and produce electron-hole pairs within the photoactive material below. Accordingly, the conductive contact has a thickness sufficient to support an electric field to drive charges to the charge conduction region for each pixel, but not so thick as to prevent (sufficient) X-rays from passing through it.

In accordance with the present invention, it has been found that it is possible to grow CdTe under low substrate temperature conditions (less than 350 degrees Celsius substrate temperature) benign to CMOS electronics. In addition, the polycrystalline structure provides strain relief, which allows for growth on materials of very different lattice spacing, such as CdTe on silicon, and growth on top of irregular surfaces, such as the surface of a silicon substrate upon which electronic circuitry has been created.

Laboratory measurements have demonstrated that polycrystalline CdTe grown under such conditions retains much of the photoelectrical properties of the single crystalline form, demonstrating that crystal boundaries and other defects do not significantly degrade the electrical properties compared to the pure single crystalline form. For example, the impedance of samples of polycrystalline grown in labs was greater than $10^6$ ohms-cm, similar to that single crystal CdTe. In addition, testing was performed for pixel uniformity using three simplified thin film CdTe (2-5 microns) pixels under a flat field illumination at 60 kV (typical dental X-ray energy levels). After only calibrating for differences in gain and no other mitigation for readout noise, a ratio of mean intensity to standard deviation (i.e., SNR) of greater than 30:1 was obtained, which is comparable to that of traditional indirect capture devices.

It has also been demonstrated in the laboratory that X-ray photon capture efficiency for an array of pixels consisting of polycrystalline-based photoresistors grown on highly doped n-type silicon is comparable to that of conventional indirect-capture X-ray imaging chips. For example, in an initial experiment on 1 mm thick slices of polycrystalline CdTe under X-ray irradiation at 60 kV and a bias of 20 V, photon capture efficiencies were obtained of approximately 33% that of those for pure CdTe. The extremely high resistance of CdTe (greater than $10^6$ ohms-cm) means the current leakage under a voltage bias is low compared to photonic induced conduction. Also, because the interface of the photodetector with the conduction region forms a heterojunction, one can take advantage of the diode behavior to further reduce dark current. However, the present invention does not depend upon diode behavior because the dark current is highly predictable. And in radiographic applications, it is common practice to record both a 'light' and 'dark' image and then subtract the dark from the light image. Laboratory measurements of light to dark current ratios in excess of 6:1 have been achieved, a value comparable to conventional indirect-capture X-ray imaging chips.

The specific embodiment of the current invention exploits properties of polycrystalline CdTe that are found in II-VI compounds and their alloys, and that are not well appreciated by researchers in the field. Thus, the present invention is not restricted to CdTe, II-VI compounds and their alloys but also includes any other photoactive materials of similar properties; these properties include: 1) electrically benign behavior at crystal grain boundaries (i.e. no sites for charge recombination), 2) can be deposited on irregular surfaces and do not require epitaxy and, 3) such deposited films tend to be columnar in structure, biasing charge migration in the vertical direction. The current invention is a simple single die approach that involves the direct deposition of an X-ray sensitive material on conventional electronics which does not require a separate intermediate layer whose purpose is to enhance adhesion and does not require pure, single-crystal epitaxial growth.

The present invention includes, but is not limited to, the following specifically preferred devices:

1. A device comprised of an integrated charge storage, amplification, and readout circuit serving as a depositional substrate with a surface exhibiting an irregular surface; and a polycrystalline photoactive material deposited as a single continuous depositional layer on top of the integrated charge storage, amplification, and readout circuit; wherein the polycrystalline photoactive material is comprised of a II-VI semiconductor compound or alloys of II-VI compounds.

2. Device 1 wherein the integrated charge storage, amplification, and readout circuit is a thin film array.

3. Device 1 the integrated charge storage, amplification, and readout circuit is silicon based.

4. Device 1 wherein the II-VI semiconductor compound is selected from the group consisting of CdTe, $Hg_xCd_{(1-x)}Te$, and $Zn_xCd_{(1-x)}Te$.

5. Device 4 wherein the II-VI semiconductor compound is CdTe.

6. Device 1 wherein the periodic pattern is comprised of a non-planar surface with two or more alternating elevations at a minimum of difference of at least approximately 0.1 microns.

7. Device 1 wherein the periodic pattern is comprised of a non-planar surface with two or more alternating elevations at a maximum of difference of approximately 100 microns.

8. Device 1 wherein the prescribed size has a distance of repetition of at least approximately 1 micron.

9. Device 1 wherein the prescribed size has a distance of repetition of at most 100 microns.

10. Device 1 wherein the single continuous depositional layer has a total surface area which exceeds 100 square millimeters.

11. Device 1 wherein the single continuous depositional layer has a total surface area which exceeds 500 square millimeters.

12. Device 1 wherein the periodic pattern is detectable by diffraction effects, such as a diffraction pattern.

13. Device 1 wherein propagation of cracks within the polycrystalline photoactive material is disrupted by the periodic pattern.

14. Device 1 wherein delamination of the polycrystalline photoactive material from the surface of the depositional substrate is inhibited by the periodic pattern.

The present invention includes, but is not limited to, the following specifically preferred processes:

1. A process, comprising: depositing a single continuous depositional layer of a polycrystalline photoactive material on an integrated charge storage, amplification, and readout circuit with an irregular surface; wherein the polycrystalline photoactive material is comprised of a II-VI semiconductor compound or alloys of II-VI compounds.

2. Process 1 wherein the prescribed size has a distance of repetition of at most 100 microns.

3. Process 1 wherein the single continuous depositional layer has a total surface area which exceeds 100 square millimeters.

4. Process 1 wherein the single continuous depositional layer has a total surface area which exceeds 500 square millimeters.

5. Process 1 wherein the single continuous depositional layer is deposited on the integrated charge storage, amplification, and readout circuit at a temperature which is not destructive to the integrated charge storage, amplification, and readout circuit.

6. Process 1 wherein the single continuous depositional layer is deposited on the integrated charge storage, amplification, and readout circuit at a temperature which does not exceed approximately 350 degrees Celsius.

7. Process 1 wherein the single continuous depositional layer is deposited on the integrated charge storage, amplification, and readout circuit at a temperature which does not exceed approximately 200 degrees Celsius.

8. Process 1 wherein the single continuous depositional layer is deposited on the integrated charge storage, amplification, and readout circuit at a depositional rate which exceeds approximately 6 microns per hour.

9. Process 1 wherein the single continuous depositional layer is deposited on the integrated charge storage, amplification, and readout circuit at a depositional rate which exceeds approximately 1 micron per hour.

10. Process 1 wherein the single continuous depositional layer of the polycrystalline photoactive material is deposited on an integrated charge storage, amplification, and readout circuit without techniques using interim substrates such as bump bonding.

11. Process 1 wherein the single continuous depositional layer of the polycrystalline photoactive material is deposited on an integrated charge storage, amplification, and readout circuit without the use of a separate intermediate layer whose purpose is to enhance adhesion.

12. Process 1 wherein the single continuous depositional layer of the polycrystalline photoactive material is deposited on an integrated charge storage, amplification, and readout circuit without the use of a compliant layer.

The present invention includes, but is not limited to, a specifically preferred sensor useful for detecting X-ray photons comprised of a silicon-based single die, charge storage, amplification, and readout pixel array integrated circuit serving as a depositional substrate with a surface exhibiting a periodic pattern of a prescribed size; and a polycrystalline photoactive material deposited as a single continuous depositional layer on top of the integrated charge storage, amplification, and readout circuit; wherein the periodic pattern is comprised of a non-planar surface with two or more alternating elevations at a minimum difference of at least approximately 0.1 micron and a maximum difference of approximately 100 microns while the prescribed size has a distance of repetition of at least approximately 1 micron but at most 100 microns; wherein the polycrystalline photoactive material is selected from the group consisting of CdTe, $Hg_xCd_{(1-x)}Te$, and $Zn_xCd_{(1-x)}Te$; and wherein the single continuous depositional layer has a total surface area which exceeds 500 square millimeters.

Specifically preferred embodiments of the current invention exploit properties of polycrystalline CdTe that are found in II-VI compounds and their alloys, and that are not well appreciated by researchers in the field. Thus, the present invention is not restricted to CdTe, II-VI compounds and their alloys but also includes any other photoactive materials of similar properties; these properties include: 1) electrically benign behavior at crystal grain boundaries (i.e. no sites for charge recombination), 2) can be deposited on irregular surfaces and do not require epitaxy and, 3) such deposited films tend to be columnar in structure, biasing charge migration in the vertical direction. It is specifically contemplated, although not yet tested in the laboratory, that the current invention can also use a layer which is a member of the class of compounds known as perovskites. This is the family of methyl ammonium lead halides, compounds with the perovskite structure and are also semiconductors. These include, methyl ammonium lead iodide, methyl ammonium lead bromide and methyl ammonium lead chloride, and use of such layers, rather than polycrystalline CdTe compounds, are specifically included as being within the scope of the present invention. The current invention is a simple single die approach that involves the direct deposition of an X-ray sensitive material on conventional electronics, and does not require pure, single-crystal epitaxial growth. Experiments confirm the feasibility of the present invention.

Accordingly, it will be apparent to those skilled in the art that still further changes and modifications in the actual concepts described herein can readily be made without departing from the spirit and scope of the disclosed inventions.

What is claimed is:

1. A device comprised of an integrated charge storage, amplification, and readout circuit serving as a depositional substrate with an irregular surface; and a polycrystalline photoactive material deposited as a single continuous depositional layer on top of the irregular surface; wherein the polycrystalline photoactive material is comprised of a II-VI semiconductor compound or alloys of II-VI compounds and the irregular surface is comprised of variations in elevation.

2. The device of claim 1 wherein the integrated charge storage, amplification, and readout circuit is a thin film array.

3. The device of claim 1 wherein the integrated charge storage, amplification, and readout circuit is silicon-based.

4. The device of claim 1 wherein the II-VI semiconductor compound is selected from the group consisting of CdTe, $Hg_xCd_{(1-x)}Te$, and $Zn_xCd_{(1-x)}Te$.

5. The device of claim 4 wherein the II-VI semiconductor compound is CdTe.

6. The device of claim 1 wherein the periodic pattern is comprised of a non-planar surface with two or more alternating elevations at a minimum of difference of at least approximately 0.1 microns.

7. The device of claim 1 wherein the periodic pattern is comprised of a non-planar surface with two or more alternating elevations at a maximum of difference of approximately 100 microns.

8. The device of claim 1 wherein the prescribed size has a distance of repetition of at least approximately 1 micron.

9. The device of claim 1 wherein the prescribed size has a distance of repetition of at most 100 microns.

10. The device 1 wherein the single continuous depositional layer has a total surface area which exceeds 100 square millimeters.

11. The device of claim 1 wherein the single continuous depositional layer has a total surface area which exceeds 500 square millimeters.

12. The device of claim 1 wherein the periodic pattern is detectable by diffraction effects, such as a diffraction pattern.

13. The device of claim 1 wherein propagation of cracks within the polycrystalline photoactive material is disrupted by the periodic pattern.

14. The device of claim 1 wherein delamination of the polycrystalline photoactive material from the surface of the depositional substrate is inhibited by the periodic pattern.

15. The device of claim 1 wherein the periodic pattern is comprised of a waffle shape.

16. The device of claim 15 wherein the waffle shape has a plurality of undercuts in a plurality of walls of the waffle shape.

17. A process, comprising depositing a single continuous depositional layer of a polycrystalline photoactive material on an integrated charge storage, amplification, and readout circuit exhibiting an irregular surface;

wherein the polycrystalline photoactive material is comprised of a II-VI semiconductor compound or alloys of II-VI compounds and the irregular surface is comprised of variations in elevation.

18. The process of claim 17 wherein the prescribed size has a distance of repetition of at most 100 microns.

19. The process of claim 17 wherein the single continuous depositional layer has a total surface area which exceeds 100 square millimeters.

20. The process of claim 17 wherein the single continuous depositional layer has a total surface area which exceeds 500 square millimeters.

21. The process of claim 17 wherein the single continuous depositional layer is deposited on the integrated charge storage, amplification, and readout circuit at a temperature which is not destructive to the integrated charge storage, amplification, and readout circuit.

22. The process of claim 17 wherein the single continuous depositional layer is deposited on the integrated charge storage, amplification, and readout circuit at a temperature which does not exceed approximately 350 degrees Celsius.

23. The process of claim 17 wherein the single continuous depositional layer is deposited on the integrated charge storage, amplification, and readout circuit at a temperature which does not exceed approximately 200 degrees Celsius.

24. The process of claim 17 wherein the single continuous depositional layer is deposited on the integrated charge storage, amplification, and readout circuit at a depositional rate which exceeds approximately 6 microns per hour.

25. The process of claim 17 wherein the single continuous depositional layer is deposited on the integrated charge storage, amplification, and readout circuit at a depositional rate which exceeds approximately 1 micron per hour.

26. The process of claim 17 wherein the single continuous depositional layer of the polycrystalline photoactive material is deposited on an integrated charge storage, amplification, and readout circuit without techniques using interim substrates such as bump bonding.

27. The process of claim 17 wherein the single continuous depositional layer of the polycrystalline photoactive material is deposited on an integrated charge storage, amplification, and readout circuit without the use of a separate intermediate layer whose purpose is to enhance adhesion.

* * * * *